United States Patent [19]
Kern et al.

[11] Patent Number: 6,100,032
[45] Date of Patent: Aug. 8, 2000

[54] HUMAN SMAD3 AND SMAD4 ARE SEQUENCE-SPECIFIC TRANSCRIPTION ACTIVATORS

[75] Inventors: Scott Eliot Kern, Hunt Valley; Leigh Zawel, Bowie; Jia Le Dai, Owings Mills; Bert Vogelstein, Baltimore; Kenneth W. Kinzler, BelAir, all of Md.

[73] Assignee: Johns Hopkins University, Baltimore, Md.

[21] Appl. No.: 09/041,675

[22] Filed: Mar. 13, 1998

[51] Int. Cl.⁷ ............................................. C12Q 1/68
[52] U.S. Cl. ............................ 435/6; 435/320.1; 536/24.1
[58] Field of Search ....................... 536/24.1; 435/6, 435/320.1

[56] References Cited

U.S. PATENT DOCUMENTS

| | | | |
|---|---|---|---|
| 5,168,499 | 12/1992 | Peterson et al. | 371/11.3 |
| 5,712,097 | 1/1998 | Kern et al. | 435/6 |

OTHER PUBLICATIONS

Kinzler et al. "Whole genome PCR: application to the identiification of sequences bound by gene regulatory proteins" Nucleic Acids Research vol. 17, No. 10, 1989, pp. 3645–3853.

Arnold R. Oliphant et al. "Defining the Sequence Specificity of DNA–Binding Proteins by Selecting Binding Sites from Random–Sequence Oligonucleotides: Analysis of Yeast GCN4 Protein" Molecular and Cellular Biology, Jul. 1989, pp. 2944–2949.

*Primary Examiner*—James Ketter
*Attorney, Agent, or Firm*—Banner & Witcoff, Ltd.

[57] ABSTRACT

Two human Smad proteins (Smad3 and Smad4) specifically recognize an identical 8 bp palindromic sequence (GTCTAGAC) (SEQ ID NO: 1). Tandem repeats of this palindrome confer striking TGF-β responsiveness to a minimal promoter. This responsiveness is abrogated by targeted deletion of the cellular Smad4 gene. DNA molecules comprising the 8 bp palindromic sequence can be used in assays for drug screening and diagnostically.

57 Claims, 6 Drawing Sheets

FIG. 1D

| Clone # | G | T | C | A | % Shifted |
|---|---|---|---|---|---|
| 1 | - | - | - | c | 43 |
| 9 | - | - | g | - | 33 |
| 13 | - | - | - | g | 31 |
| 14 | - | - | a | a | 31 |
| 2 | - | - | t | - | 29 |
| 7 | - | - | c | t | 29 |
| 5 | - | - | - | t | 26 |
| 6 | - | - | t | g | 25 |
| 10 | - | - | t | - | 23 |
| 12 | - | - | g | a | 23 |
| 3 | - | t | c | t | 22 |
| 8 | - | c | c | g | 11 |
| 4 | - | - | c | a | 4 |
| 11 | - | - | g | a | 1 |

FIG. 1B

| Clone # | G | T | C | A | % Shifted |
|---|---|---|---|---|---|
| 32 | - | - | - | - | 49 |
| 7 | - | - | - | t | 41 |
| 14 | - | - | - | c | 39 |
| 23 | - | - | - | - | 39 |
| 6 | - | - | - | g | 30 |
| 18 | - | - | g | t | 30 |
| 17 | - | - | - | c | 29 |
| 9 | - | - | - | g | 25 |
| 16 | - | - | - | c | 21 |
| 13 | - | - | g | c | 19 |
| 10 | - | - | - | c | 19 |
| 12 | - | - | t | g | 18 |
| 15 | - | t | - | - | 16 |
| 11 | - | - | c | g | 8 |

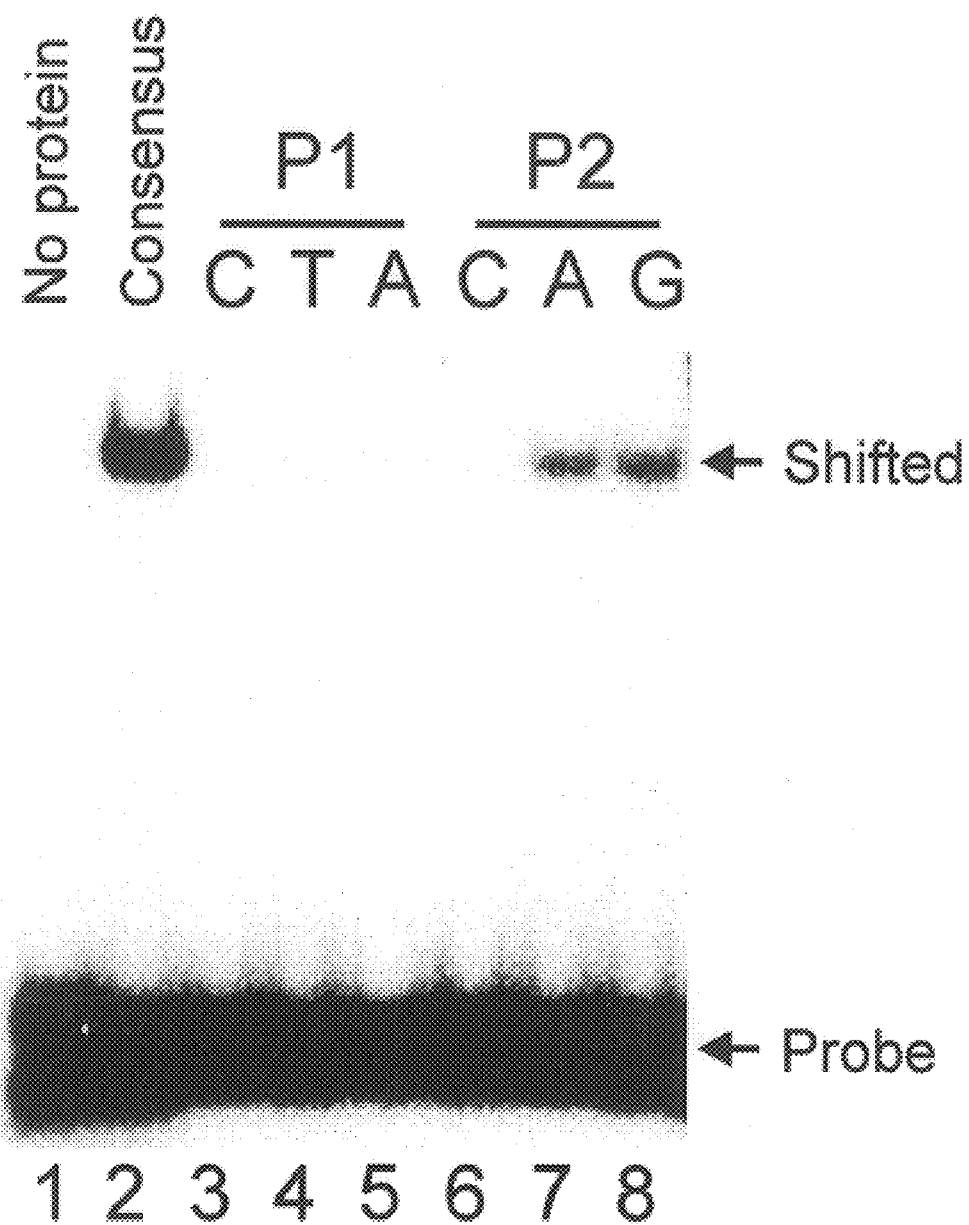

FIG. 4

TABLE 1. Consensus Binding to Smad Proteins

A. Relative Efficiency of Substituted SBE Oligonucleotides

| Base at Indicated Position | Consensus Position | | | | | | | |
|---|---|---|---|---|---|---|---|---|
| | 1 | 2 | 3 | 4 | 5 | 6 | 7 | 8 |
| G | 100/100 | 33/63 | 7/9 | 5/9 | 7/17 | 100/100 | 7/31 | 2/3 |
| A | 5/11 | 19/57 | 2/6 | 2/3 | 100/100 | 2/3 | 100/100 | 14/29 |
| T | 2/4 | 100/100 | 7/17 | 100/100 | 2/3 | 5/6 | 57/51 | 2/3 |
| C | 2/3 | 5/23 | 100/100 | 6/11 | 2/3 | 5/6 | 7/26 | 100/100 |

B. Base Frequencies in Captured Clones

| Protein | Consensus Position | | | | | | | |
|---|---|---|---|---|---|---|---|---|
| | G | T | C | T | A | G | A | C |
| GST-Smad3/MH1 | 100% | 100% | 100% | 86% | 20% | 86% | 33% | 40% |
| GST-Smad4/MH1 | 100% | 100% | 100% | 85% | 63% | 89% | 31% | 89% |
| GST-Smad4/FL | 100% | 93% | 100% | 96% | 79% | 100% | 43% | 68% |

(A) The fraction of each probe bound to Smad4 (left of slash) or Smad3 (right of slash) is indicated, as determined by EMSA. Results are normalized to the results obtained with SBE, containing the consensus sequence.
(B) The fraction of clones containing the consensus nucleotide at the indicated position is shown. 19, 26, and 28 clones were evaluated for Smad3/MH1, Smad4/MH1, and Smad4/FL, respectively.

SEQUENCE LISTING

```
<160> NUMBER OF SEQ ID NOS: 27

<210> SEQ ID NO 1
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 1 gtctagac                                                                  8

<210> SEQ ID NO 2
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 2 gtctcgtc                                                                  8

<210> SEQ ID NO 3
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 3 gtctagtc                                                                  8

<210> SEQ ID NO 4
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 4 gtctagcc                                                                  8

<210> SEQ ID NO 5
<211> LENGTH: 8
```

-continued

```
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 5 gtctaggg                                                                   8

<210> SEQ ID NO 6
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 6 gtctagtc                                                                   8

<210> SEQ ID NO 7
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 7 gtcgcgcc                                                                   8

<210> SEQ ID NO 8
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 8 gtctaggc                                                                   8

<210> SEQ ID NO 9
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 9 gtctggcc                                                                   8

<210> SEQ ID NO 10
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 10 gtctagcc                                                                   8

<210> SEQ ID NO 11
<211> LENGTH: 8
<212> TYPE: DNA
```

-continued

```
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 11 gtcgcgcc                                                                  8

<210> SEQ ID NO 12
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 12 gtctcggc                                                                  8

<210> SEQ ID NO 13
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 13 gtctatac                                                                  8

<210> SEQ ID NO 14
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 14 gtccccgt                                                                  8

<210> SEQ ID NO 15
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 15 gtctgggc                                                                  8

<210> SEQ ID NO 16
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 16 gtctagac                                                                  8

<210> SEQ ID NO 17
<211> LENGTH: 8
<212> TYPE: DNA
<213> ORGANISM: Artificial Sequence
```

```
<220> FEATURE:
<223> OTHER INFORMATION: synthetic random oligonucleotides selected for
      binding to human SMAD3 or human SMAD4

<400> SEQUENCE: 17 gtctgata                                                                      8

<210> SEQ ID NO 18
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 18 gtctggat                                                                      8

<210> SEQ ID NO 19
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 19 gtctggct                                                                      8

<210> SEQ ID NO 20
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 20 gtctggat                                                                      8

<210> SEQ ID NO 21
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 21 gtctggtg                                                                      8

<210> SEQ ID NO 22
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 22 gtctcatt                                                                      8

<210> SEQ ID NO 23
<211> LENGTH: 8
<212> TYPE: DNA
<213> ORGANISM: Artificial Sequence
<220> FEATURE:
```

```
<223> OTHER INFORMATION: synthetic random oligonucleotides selected for
      binding to human SMAD3 or human SMAD4

<400> SEQUENCE: 23 gtctgggc                                                                    8

<210> SEQ ID NO 24
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 24 gtctggct                                                                    8

<210> SEQ ID NO 25
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 25 gcttagag                                                                    8

<210> SEQ ID NO 26
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 26 gtccctca                                                                    8

<210> SEQ ID NO 27
<211> LENGTH: 8
<212> TYPE: DNA
<213> ORGANISM: Artificial Sequence
<220> FEATURE:
<223> OTHER INFORMATION: synthetic random oligonucleotides selected for
      binding to human SMAD3 or human SMAD4

<400> SEQUENCE: 27 gtctggga                                                                    8
```

HUMAN SMAD3 AND SMAD4 ARE SEQUENCE-SPECIFIC TRANSCRIPTION ACTIVATORS

This invention was made using funding from the National Institutes of Health, grant numbers CA43460, CA82924, and CA68228. The federal government therefore retains certain rights in this invention.

TECHNICAL FIELD OF THE INVENTION

This invention is related to the field of gene regulation. In particular it is related to the field of regulating genes using TGF-β.

BACKGROUND OF THE INVENTION

TGF-β is the prototype of a family of structurally related cytokines capable of inducing diverse cellular responses, including apoptosis, differentiation, and cell cycle arrest. Cancer cells often lose responsiveness to TGF-β, an event which apparently affords a growth advantage and favors tumor progression. The fact that components of the TGF-β signaling pathway are mutated in cancers provides compelling support for this idea. In this regard, mutations in the TGF-β receptor type II gene are prevalent in cancers with mismatch repair deficiency, Smad4 mutations commonly occur in pancreatic carcinomas, and Smad4 and Smad2 mutations are found in a subset of colorectal cancers.

Two types of TGF-β receptor (TGF-βR), each containing an intracellular serine/threonine kinase domain, act in concert to activate signaling. TGF-βRII binds TGF-β and subsequently phosphorylates TGF-βRI. The activated RI receptor then propagates the signal by phosphorylating intracellular targets, the most important of which in mammalian cells appear to be the Smad proteins. The Smad genes are homologues of Drosophila and C. elegans genes identified as critical mediators of TGF-β-like signaling. In vertebrate cells, Smads 1, 2, 3 and 5 are phosphorylated by activated RI receptors at a conserved SSXS motif located at their carboxyl termini, whereupon they translocate from the cell membrane or cytoplasm to the nucleus. Smad4 (a.k.a. DPC4) lacks the signature phosphorylation site at its C-terminus and has not been found to associate with the TGF-βR complex. Instead, Smad4 forms heteromeric complexes with other Smads after ligand stimulation and may be important for their translocation to the nucleus.

In mammalian cells, Smad2 and Smad3 are phosphorylated upon TGF-β stimulation while Smad1 is phosphorylated in response to BMP. Once heterodimerized with Smad4 and transported to the nucleus, the mechanisms through which Smad proteins propagate TGF-β signaling are unclear. When expressed as fusion proteins with Gal4, the carboxyl-terminal domains of Smad proteins confer transcriptional activation to reporters containing Gal4-binding sequences. Smad proteins can complex with Xenopus FAST-1, a protein which possesses a DNA-binding domain. These observations have suggested that a complex composed of Smad proteins and FAST-1 may transcriptionally activate promoters containing DNA sequences recognized by the latter protein. More recently, it has been shown that the amino-terminal domain of Drosophila Mad can itself bind to elements within the vestigal (Vg) promoter, suggesting a sequence-specific binding function that might directly account for the biologic activity of the Mad protein. However, the full length Drosophila Mad protein did not exhibit DNA-binding activity, raising questions about the role of this binding in vivo. In another study, human Smad4, but not Smad3, was shown to bind to sequences from p3TP-lux, a reporter commonly used to assess TGF-β responses. Interestingly, the sequences responsible for binding of Drosophila Mad to the Vg promoter bore little resemblance to the p3TP-lux elements that bound to Smad4. Additionally, the sequences within p3TP-lux that bound to Smad4 were completely dispensable for TGF-β-dependent activation of this reporter.

SUMMARY OF THE INVENTION

According to one embodiment of the invention applicants provide an isolated subgenomic polynucleotide comprising a SMAD binding element as shown in any of SEQ ID NOs: 1–29, as shown in FIGS. 1B and 1D.

According to another embodiment of the invention a nucleic acid construct is provided. The construct comprises at least one SMAD binding element, a minimal promoter, and a reporter gene. The minimal promoter is upstream from the reporter gene. The minimal promoter regulates transcription of the reporter gene.

According to another aspect of the invention a method is provided of pre-screening agents for use in cancer therapy. Binding of a SMAD3 or SMAD4 protein to a DNA molecule comprising a sequence as shown in any of SEQ ID NOs: 1–29 is measured in the presence and absence of a test substance. The amount of binding of the SMAD3 or SMAD4 protein in the presence of the test substance is compared to the amount of binding of the SMAD3 or SMAD4 protein in the absence of the test substance. A test substance which increases the amount of binding is identified as a candidate for use in cancer therapy.

In another embodiment of the invention a method of pre-screening agents for use in cancer therapy is provided. A transfected cell is contacted with a test substance. The transfected cell contains a SMAD3 or SMAD4 protein and a reporter gene construct. The construct contains a reporter gene which encodes an assayable product, at least one copy of a SMAD binding element, and a minimal promoter which is upstream from and regulates transcription of the reporter gene. The amount of expression of the reporter gene is determined. If the amount of expression is altered by the test substance, the test substance is identified as a candidate for use in cancer therapy.

Another aspect of the invention is a method of pre-screening potential therapeutic agents. A transfected cell is contacted with a test substance and TGFβ. The transfected cell contains a SMAD3 or SMAD4 protein and a reporter gene construct. The reporter gene construct comprises a reporter gene which encodes an assayable product, at least one copy of a SMAD binding element, and a minimal promoter which is upstream from and regulates transcription of the reporter gene. The amount of expression of the reporter gene is determined. A test substance which decreases the amount of expression of the reporter gene is identified as a candidate for inhibiting apoptosis.

Another method of pre-screening agents for use in cancer therapy is provided by the invention. RNA polymerase and ribonucleotides are added to a transcription construct in the presence and absence of a test substance. The transcription construct comprises a reporter gene which encodes an assayable product, a minimal promoter, and at least one copy of a SMAD binding element. The minimal promoter is upstream from and controls transcription of the reporter gene. The amount of transcription of the reporter gene is altered by the presence of the test substance, a test substance which alters the amount of transcription of the reporter gene being a candidate for use in cancer therapy.

Another embodiment of the invention provides a method of prescreening oligonucleotides for use in cancer therapy. A SMAD3 or SMAD4 protein which is encoded by a mutant gene found in a cancer patient is added to a preparation of random oligonucleotides and a DNA fragment comprising at least one copy of a SMAD binding element. The DNA fragment is immobilized on a solid support. Conditions are those in which wild-type SMAD3 or SMAD4 protein binds to the DNA fragment immobilized on a solid support. Oligonucleotides are recovered from the preparation which bound to SMAD3 or SMAD4 which bound to the DNA fragment immobilized on the solid support.

In another embodiment of the invention a method is provided for detecting the presence of wild-type SMAD3 or SMAD4 protein in a cell. A DNA molecule comprising at least one SMAD binding element is contacted with a cell lysate from a tissue of a human, under conditions in which the DNA molecule binds to wild-type SMAD3 or SMAD4. The presence of wild-type SMAD3 or SMAD4 protein in the cell is determined by detecting binding of the proteins to the DNA molecule.

Another aspect of the invention is another technique for detecting the presence of a wild-type SMAD3 or SMAD4 protein in a cell. A histological section from a human is incubated with a detectably-labeled DNA molecule which contains at least one SMAD binding element. The incubation is performed under conditions in which the DNA molecule binds to wild-type SMAD3 or SMAD4. Unbound DNA molecules are removed from the histological section. The amount of DNA molecule which is bound to the histological sample is determined.

According to still another aspect of the invention, a method of is provided of identifying compounds which specifically bind to a SMAD binding element. A DNA molecule comprising at least one SMAD binding element as shown in any of SEQ ID NOs: 1–29 is contacted with a test compound, to bind the test compound to the DNA molecule. The amount of test compound which is bound to the DNA molecule is determined. Compounds which bind to the binding element are candidate drugs for substituting for TGF-β.

Another aspect of the invention provides yet another method of identifying compounds which specifically bind to SMAD binding elements. An immobilized DNA molecule comprising a SMAD binding element is contacted with both a test compound and wild-type SMAD3 or SMAD4 protein to bind the wild-type SMAD3 or SMAD4 protein to the DNA molecule. The amount of wild-type SMAD3 or SMAD4 protein which is bound to the DNA molecule is determined. Inhibition of binding of wild-type SMAD3 or SMAD4 protein by the test compound is an indication of binding of the test compound to the SMAD binding element.

Another aspect of the invention is a method for detecting a SMAD3 or SMAD4 gene in a human cell. A nucleic acid molecule encoding a SMAD3 or SMAD4 protein is obtained from a human cell. A SMAD3 or SMAD4 protein is then expressed from the nucleic acid molecule. The expressed SMAD3 or SMAD4 protein is contacted with a reporter construct comprising: at least one SMAD binding element, a minimal promoter, and a reporter gene. The minimal promoter is upstream from the reporter gene and the minimal promoter regulates transcription of the reporter gene. Expression of the product of the reporter gene is monitored.

Yet another embodiment of the invention is another method for detecting a SMAD3 or SMAD4 gene in a human cell. A nucleic acid molecule encoding a SMAD3 or SMAD4 protein is obtained from a human cell. A SMAD3 or SMAD4 protein is expressed from the nucleic acid molecule. The expressed SMAD3 or SMAD4 protein is contacted with an isolated subgenomic polynucleotide comprising a SMAD binding element. The binding of the expressed SMAD3 or SMAD4 to the isolated subgenomic polynucleotide is monitored.

These and other embodiments of the invention which are described in more detail below, provide the art with diagnostic tools and drug discovery methods which are useful in the campaign against cancer.

BRIEF DESCRIPTION OF THE DRAWINGS

FIGS. 1A–1D. Analysis of clones containing Smad-binding sequences (FIG. 1A) Representative examples of EMSA of labeled PCR products derived from mock-selected or Smad4-selected clones. Equal amounts of each PCR product were added to the same amount of GST-Smad4/MH1 fusion protein, and EMSA performed as described in Experimental Procedures. For unknown reasons, two, differently-migrating complexes containing Smad4 proteins and DNA were usually observed upon EMSA.

(FIG. 1B) Oligonucleotide sequences of representative Smad4-selected clones, aligned according to the consensus shown at the top. The EMSA binding efficiency of each clone (amount of oligonucleotide in DNA-protein complexes divided by amount added to the reaction) is shown for each clone. Dashes indicate matches to the consensus. Clones are listed in decreasing order of binding efficiency. Clone 32 corresponds to SEQ ID NO: 1. Clone 7 corresponds to SEQ ID NO:2. Clone 14 corresponds to SEQ ID NO: 3. Clone 23 corresponds to SEQ ID NO: 4. Clone 6 corresponds to SEQ ID NO: 5. Clone 18 corresponds to SEQ ID NO: 6. Clone 17 corresponds to SEQ ID NO: 7. Clone 9 corresponds to SEQ ID NO: 8. Clone 16 corresponds to SEQ ID NO: 9. Clone 13 corresponds to SEQ ID NO: 10. Clone corresponds to SEQ ID NO: 11. Clone 12 corresponds to SEQ ID NO: 12. Clone 15 corresponds to SEQ ID NO: 13. Clone 11 corresponds to SEQ ID NO: 14.

(FIG. 1C) EMSA of labeled PCR products derived from representative GST-Smad3/MH1-selected clones, performed as described in (FIG. 1A).

(FIG. 1D) Oligonucleotide sequences of representative Smad3-selected clones, aligned according to the consensus shown at the top. The EMSA binding efficiency of each clone was determined as in (FIG. 1A). Clone 1 corresponds to SEQ ID NO: 1. Clone 9 corresponds to SEQ ID NO: 15. Clone 13 corresponds to SEQ ID NO: 16. Clone 14 corresponds to SEQ ID NO: 17. Clone 2 corresponds to SEQ ID NO: 18. Clone 7 corresponds to SEQ ID NO: 19. Clone 5 corresponds to SEQ ID NO: 20. Clone 6 corresponds to SEQ ID NO: 21. Clone 10 corresponds to SEQ ID NO: 22. Clone 12 corresponds to SEQ ID NO: 23. Clone 3 corresponds to SEQ ID NO: 24. Clone 8 corresponds to SEQ ID NO: 25. Clone 4 corresponds to SEQ ID NO: 26. Clone 11 corresponds to SEQ ID NO: 27.

FIG. 2A and 2B. Binding of SBE oligonucleotides to Smad proteins (FIG. 2A) Examples of EMSA using GST-Smad3/H1 and a $^{32}$P-labeled SBE probe (lanes 1 and 2) or similar probes in which a single nucleotide was substituted for one of the consensus positions. In lanes 3–5 and 6–8, the indicated nucleotides were substituted for G and T at positions 1 and 2, respectively.

(FIG. 2B) The $^{32}$P-labeled SBE probe was incubated with 0.6 ug of a fusion protein containing either the MH1 domain of Smad4 (lane 1) or 0.4–1.6 ug of a fusion protein containing FL Smad4 (lanes 2–5).

(FIG. 3B) HCT116 cells ("Smad4+/+"), or a derivative in which the Smad4 gene had been deleted through homologous recombination ("Smad4−/−"), were co-transfected in the presence of TGF-β with SBE4-luc and with or without the TGF-β RII expression vector, as indicated. Grouped bars represent luciferase measurements from the same constructs in three separate experiments.

FIG. 4A and 4B. Consensus binding sequence to SMAD proteins.

FIG. 4A. Relative efficiency of substituted SBE oligonucleotides.

FIG. 4B. Base frequencies in captured clones.

DETAILED DESCRIPTION

Figures 1A, 1C:
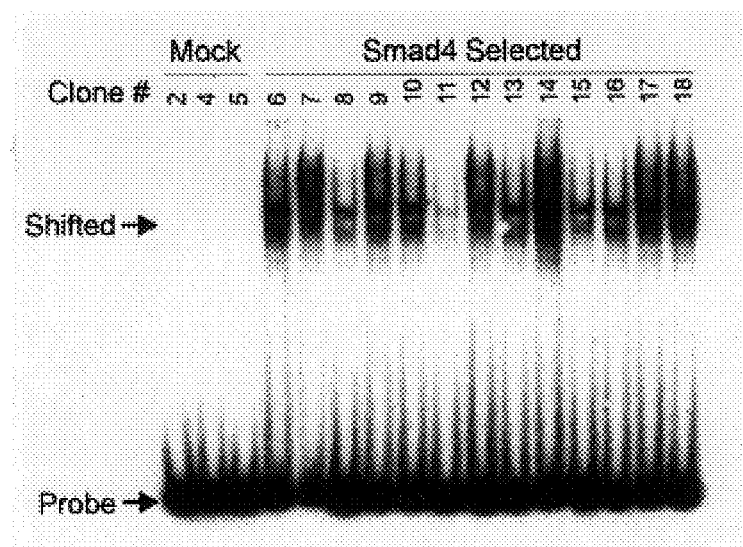

To clarify the DNA-binding capabilities of human Smads 2, 3, and 4, we have investigated their ability to bind to the Vg promoter as well as to other DNA sequences. The results were surprising, demonstrating that while both Smad3 and Smad4 could bind to the Vg promoter, they bound much more efficienfly to an unrelated octameric sequence discovered through an unbiased approach. The consensus sequence bound by Smads 3 and 4 confer remarkable TGF-β-dependent responsiveness to a minimal promoter in vivo, and this responsiveness is dependent on the presence of the cellular Smad4 gene.

A minimally active promoter, according to the present invention, is a promoter which is not transcribed or is transcribed at a very low level in the absence of an inducer. Many such promoters are known in the art and include the minimal CMV promoter (Boshart et al. (1985) Cell 41: 521–30) and the promoters for TK (Nordeen (1988) BioTechniques 6: 454–48), IL-2, and MMTV.

Although one particular octamer (SEQ ID NO: 1) has been found to have the optimal binding ability to SMAD3 and SMAD4, other sequences (SEQ ID NOs:2–29) have been found to function to differing extents. See FIGS. 1B and 1D. Isolated subgenomic polynucleotides are provided which comprise at least one SMAD binding element (SBE) as shown in any of SEQ ID NOs:1–29. Such polynucleotides contain the SBE in a context which is different than in the human genome. Thus the SBE will be isolated away from other sequences to which it is naturally contiguous, or it will be adjacent to different sequences than in nature. The SBE may be multimerized, i.e., in tandem arrays of two, three, four, or more octamers. The octamers may be immediately adjacent, or may be spaced by other nucleotides of between 1 and 10, 10 and 20, or 20 and 50 nucleotides. Preferably the polynucleotide will be double stranded, although single stranded polynucleotides may also be used.

According to certain embodiments of the invention the polynucleotide will preferably be attached to a solid support, either by an affinity interaction, or by a covalent bond. Solid supports may include filters, beads, polymers, column packing matrices, etc. In one particular embodiment an insoluble polymer is used as a solid support. Immobilization of SBEs to a solid or insoluble support can be used to readily separate unbound from bound SMAD proteins using a simple phase separation.

The SBEs according to the present invention are able to mediate two biological reactions. They bind SMAD3 and SMAD4, and they are able to confer TGF-β inducibility on a minimal promoter. Although some particular SBEs are disclosed herein, other SBEs can be used as well. These can be identified using routine techniques for design and synthesis of oligonucleotides and routine assays for biological function. SBEs according to the present invention preferably have at least 4, 5, 6, or 7 nucleotides in common with the optimal octamer. Preferably they retain at least one third of the biological activity of the octamer, and more preferably at least two thirds. However, octamers with lower levels of activity may be useful to screen for compounds which enhance the binding of SMAD3 or SMAD4 to their natural DNA sequences. As shown in FIG. 4, certain residues of the octamer are more important for maintaining biological function than others. Thus consensus positions 2 and 7 are most tolerant of changes. Position 8 is also fairly tolerant of change if the change is from a C to an A.

Given the ability of the SBEs to create TGF-β sensitivity, it is desirable to make and use constructs comprising the SBE so that inter alia compounds and other substances can be screened for the ability to enhance or diminish TGF-β-mediated effects. One particularly useful construct employs at least one SMAD binding element as shown in any of SEQ ID NOs: 1–29, a minimal promoter, and a reporter gene. The minimal promoter is upstream from the reporter gene, and the minimal promoter regulates transcription of the reporter gene. The construct may comprise tandem repeats of the SBE, containing at least two, three, or four copies of the SBE. Such constructs can be used to assay for effects on components of TGF-β regulated pathways, including on SMAD3 and SMAD4. Substances can be screened for the ability to induce, inhibit, or substitute for TGF-β. Such assays can be performed in a cell-free system, in transfected cells in vitro, and in mammals which have cells transfected with such reporter constructs. SMAD3 or SMAD4 which is used in such assays can be wild-type or mutants which occur in cancer cells. Thus substances can be screened for the ability to restore wild-type binding or induction to mutant SMAD3 or SMAD4 proteins.

Reporter genes for use in the present invention are any which are convenient to assay. These include, without limitation, genes encoding luciferase, β-galactosidase, chloramphenicol acetyl transferase, and neomycin phosphotransferase. The products of these enzymes can be assayed or monitored as is known in the art and conventional.

As discussed above, the SBE mediates two distinctly assayable biological functions: binding of SMAD3 and SMAD4 and TGF-β mediated inducibility. Either of these functions can form the basis of assays for screening potential therapeutic agents and for assaying cells or tissues for the status of the SMAD3 or SMAD4 genes. Agents which enhance binding or inducer activity of SBEs are candidate therapeutic agents for treating cancer. Agents which inhibit binding are candidate therapeutic agents for inhibiting apoptosis. Such agents may be desirable for treatment of cells that are dying prematurely in a disease state such as Alzheiner's Disease, AIDS, muscular dystrophy, amyotrophic lateral sclerosis, or other muscle wasting diseases, autoimmune diseases, or a disease in which cells are infected with a pathogen such as a virus, bacterium, fungus, mycoplasm, or protozoan.

The biological functions of SBEs can be used to screen cells for wild-type or mutant versions of SMAD3 or SMAD4, proteins or genes. The proteins may be isolated from cells and tested directly. Alternatively, nucleic acids encoding SMAD3 or SMAD4 can be isolated from cells, and used to direct synthesis of proteins, either in vitro or in vivo.

Assays for induciblity of a reporter gene can be performed in a transfected cell or in a cell-free system. If in a transfected cell, the cell comprises a reporter gene construct and is contacted with an agent to be tested, in the presence or absence of TGF β.

Substances and compounds which can be screened for their biological effect on the SBE activity include any which are previously known in the art to be therapeutic agents, or those which are unknown as such. Compounds can be organic or inorganic molecules, synthetic or natural products, purified compounds or mixtures of compounds. Libraries of compounds may be used. Particularly useful compounds may be peptides or oligonucleotides.

In binding assays, it may be desirable that the DNA molecule be labeled with a detectable moiety. Suitable detectable moieties include a radioactive moiety, a colorimetric moiety, or a fluorescent moiety. Alternatively, the SMAD3 or SMAD4 protein may be labeled. In another format, a reagent which specifically interacts with SMAD3 or SMAD4 can be labeled, such as an antibody. In another format, a second antibody which is detectably labeled may be used to bind to a first antibody which binds to SMAD3 or SMAD4.

Samples to be tested for the SMAD3 or SMAD4 genetic status may be cell lysates from tissue samples, blood or serum samples, histological samples, etc. If nucleic acids, RNA or DNA, are to be isolated and tested, then body fluids may also be used as a test sample, including urine and sputum. The genetic status can be determined by testing the proteins, or by using nucleic acids to make proteins, either in vitro or in vivo, and testing the proteins which are so made for the binding ability to SBEs or for the inducibility activity of a minimal promoter in the presence of TGF β.

The above disclosure generally describes the present invention. A more complete understanding can be obtained by reference to the following specific examples which are provided herein for purposes of illustration only, and are not intended to limit the scope of the invention.

EXAMPLE 1
The MH1 Domain of Human Smad3 and Smad4 Specifically Bind DNA

The DNA-binding activity of Drosophila Mad was found to reside in its amino-terminal MH1 domain and to be inhibited by its carboxyl-terminus. To evaluate whether the analogous domain of human Smad proteins could bind DNA, GST fusion proteins containing the MH1 domains of Smads 2, 3, and 4 were constructed and expressed in $E. coli$. Electrophoresis mobility shift assays (EMSA) were performed using the purified proteins and labeled oligonucleotides containing the optimal sequence from Vg, essentially as described by Kim et al ). We found that the MH1 domains of Smad3 and Smad4, but not of Smad2, were capable of specific binding to the Vg probe (data not shown). However, the binding was relatively inefficient, typically resulting in shifts of less than 5% of the input Vg probe. Several experimental manipulations were employed to increase the efficiency of binding (such as variations of cation, salt concentration, competitor, and other components of the binding buffer) without success.

To determine whether other DNA sequences might bind more efficiently to Smad proteins, we tested binding to a random pool of oligonucleotides, using a variation of PCR/selection strategies described earlier. The oligonucleotide was degenerate in a 20 bp central region and flanked on each side by a 20 bp region of known sequence. Smad fusion proteins were mixed with the random duplex pool and subjected to EMSA. broad region of the gel predicted to contain DNA-protein complexes (from experiments with the Vg oligonucleotide) was excised and the DNA was eluted and PCR-amplified. Following three rounds of selection and amplification, the enriched oligonucleotides were cloned. Radiolabeled probes corresponding to single clones were then generated and independently assayed by EMSA, and the sequences of clones exhibiting binding were determined.

Following selection with a GST-fusion protein containing the MH1 domain of Smad4 (GST-Smad4/MH1), thirty clones were selected for analysis. Radiolabeled probes generated from each of these clones bound to Smad4, but the efficiency of binding varied considerably (representative examples in FIG. 1A). Binding was specific, as clones isolated from a mock selection did not form complexes (FIG. 1A). Sequencing revealed that a related 8 bp sequence (5'-GTCTAGNC-3') or its complement was present in each clone (aligned in FIG. 1B). The first three positions of this consensus were completely invariant. Notably, a perfect palindrome was present in clones wherein the $7^{th}$ position was A. The only clone (#32) containing this palindromic sequence was the most efficient with respect to Smad4-binding, resulting in a shift of nearly 50% of the probe (FIG. 1B).

We next investigated Smad2 and Smad3 binding to DNA with the same approach. Nineteen of twenty Smad3-selected clones tested positively in EMSA (representative examples in FIG. 1C). Interestingly, sequence analyses with these clones revealed an identical consensus to that obtained for Smad4 (FIG. 1D). Again, the clone with the best binding matched the palindromic octamer (clone #1). Variability in binding of clones with similar octameric sequences suggested that positions outside the octamer could affect binding efficiency.

It was particularly important to perform analogous experiments with Smad2. Based on the sequence homologies between Smads 2, 3, and 4, we expected that Smad2 would also bind DNA, but the fact that Smad2 did not bind to Vg sequences or to the palindrome described above (data not shown) suggested that its binding specificity might be distinct. However, the approach outlined in FIG. 2, when applied to the MH1 domain of Smad2, revealed no specific binding to any oligonucleotide sequence within the pool. Only small quantities of the random oligonucleotides were gel-shifted by GST-Smad2/MH1, and many more PCR cycles were required to successfully amplify the recovered oligonucleotides compared to those gel-shifted by GST-Smad3/MH1 or GST-Smad4/MH1. Repeated cycles of binding and PCR did not result in significantly improved gel-shifting of the recovered oligonucleotides. To exclude the possibility that a small fraction of oligonucleotides which could specifically bind to Smad2 were present within a larger quantity of oligonucleotides non-specifically bound to Smad2, we analyzed twenty GST-Smad2/MH1-selected clones by EMSA; none were capable of forming gel-retarded complexes (data not shown).

Smad Protein Production

Smad2 (codons 1–242 in GST-Smad2/MH1), Smad3 (codons 1–200 in GST-Smad3/MH1), and Smad4 (codons 1–276 in GST-Smad4/MH1 and full-length (codons 1–570 in GST-Smad4/FL) were cloned into the BamHI site of pGEX2TK (Pharmacia) using a PCR-based approach (details available upon request). The full length Smad4 protein was also expressed as a $His_6$-fusion protein in the vector pET33b (Novagen). All constructs were validated by sequencing. Proteins were expressed and purified according to the manufacturers' protocol.

EMSA

DNA-binding assays were performed essentially as described except that poly (dI-dC), 6 ug/ml, was used as the only competitor and 2% NP-40 was included in the reaction mix. For binding to PCR products derived from clones (e.g., FIG. 1), 1.0–0.5 ug protein (~1 centration) and 50 ng of DNA end-labeled to $2\times10^6$ dpm/ug, was used. For binding to oligonucleotides, 0.3–0.5 ug of protein (~0.4 uM final concentration) and 0.5 ng of DNA end-labeled to $2\times10^8$ dpm/ug, was used. Specificity of binding was checked by competition with unlabeled SBE oligonucleotides and lack of competition with irrelevant oligonucleotides. Quantitation of binding was performed using an Instant Imager (Packard).

The sequence of the Vg probe used was
5'-TTTGTGCTTGGCTGCCGTCGCGATTCGACAACTT-TGG-3'. For binding to the MH1 domains of Smad3 and Smad4 proteins, the following oligonucleotide was synthesized:
5'-TAGTAAACACTCTATCAATTGG(N)$_{20}$GGCTGTAAACGATACTGG AC-3', with "N" representing an equimolar mixture of each nucleotide. For binding to Smad4-FL, the oligonucleotide
5'-CACTCGAGGGATCCGAATTC(N)$_{25}$TCTAGAAAGCTTGTCGACGC -3' was used. Probes for gel shift were generated using these oligonucleotides as templates and the primers
5'-TAGTAAACACTCTATCAATTGG-3' and
5'-GTCCAGTATCGTTTACAGCC-3' for the MH1 domains of Smad3 and Smad4 and the primers
5'-CACTCGAGGGATCCGAATTC-3' and
5'-GCGTCGACAAGCTTTCTAGA-3' for Smad4-FL. Following binding to ~1 ug of Smad proteins (or following "mock" reactions, without added protein), EMSA was performed and the location of the DNA-protein complexes within the gels was approximated based on the mobility of complexes generated with the Vg probe. Gel slices were homogenized, incubated at 65(C for 30 min., and passed through Spin-X columns (Costar). Recovered oligonucleotides were extracted with phenol-chloroform, precipitated with ethanol, re-amplifed, and subjected to the next round of binding. Following completion of the third selection-amplification cycle, PCR products were cloned into pZERO2. 1 (Invitrogen). Sixty bp probes corresponding to single clones were generated for EMSA by colony PCR using the following $^{32}$P-labeled primers:
5'-TAGTAAACACTCTATCAATTGG-3' and
5'-GTCCAGTATCGTTTACAGCC-3'. To determine the oligonucleotide sequences contained within single clones, inserts were amplified by colony PCR using M13 forward and reverse primers and the PCR products sequenced using the Amersham Thermosequenase kit and an SP6 primer.

In instances where complementary oligonucleotide probes were chemically synthesized (rather than generated through PCR), the oligonucleotides were labeled with g$^{32}$P-ATP andT4 polynucleotide kinase prior to annealing. The sequence of the SBE probe was 5'-GGAGTATGTCTAGACTGACAATGTAC-3'.

EXAMPLE 2

Further Definition of the Sequences Required for Binding

To confirm that the 8 bp palindrome (SBE, for Smad binding element) was sufficient for binding to Smad3 and 4, complementary 26 bp oligonucleotides containing a single SBE were synthesized and used to generate a radiolabeled probe. The SBE probe was bound by the MH1 domains of Smad3 and Smad4 to the same extent as longer probes derived by PCR from selected clones. When nucleotides at more than one position within the first three bases of the palindrome were simultaneously changed, binding was completely eliminated (data not shown).

To determine the precise sequences required for binding to Smad 3 and Smad4, oligonucleotides corresponding to all possible single base pair changes of the octameric SBE were synthesized. Most substitutions reduced binding efficiency by over 90%, though a few (largely at positions 2 and 7 of the octamer) reduced binding by only 50% (FIG. 4A; examples in FIG. 2A). Subtle differences between the binding efficiencies of Smad3 and Smad4 to certain variants were apparent in these analyses (particularly at positions 2 and 7; FIG. 4A). Importantly, no single base variant of the SBE bound better to either GST-Smad3/MH1 or GST-Smad4/MH1 than the SBE itself Experiments in which varying amounts of GST-Smad3/MH1 and GST-Smad4/MH1 were mixed together and added to labeled oligonucleotides showed that the binding efficiencies of Smad3 and Smad4 were comparable (data not shown).

EXAMPLE 3

Binding to Full Length Smad4

Figure 2B:
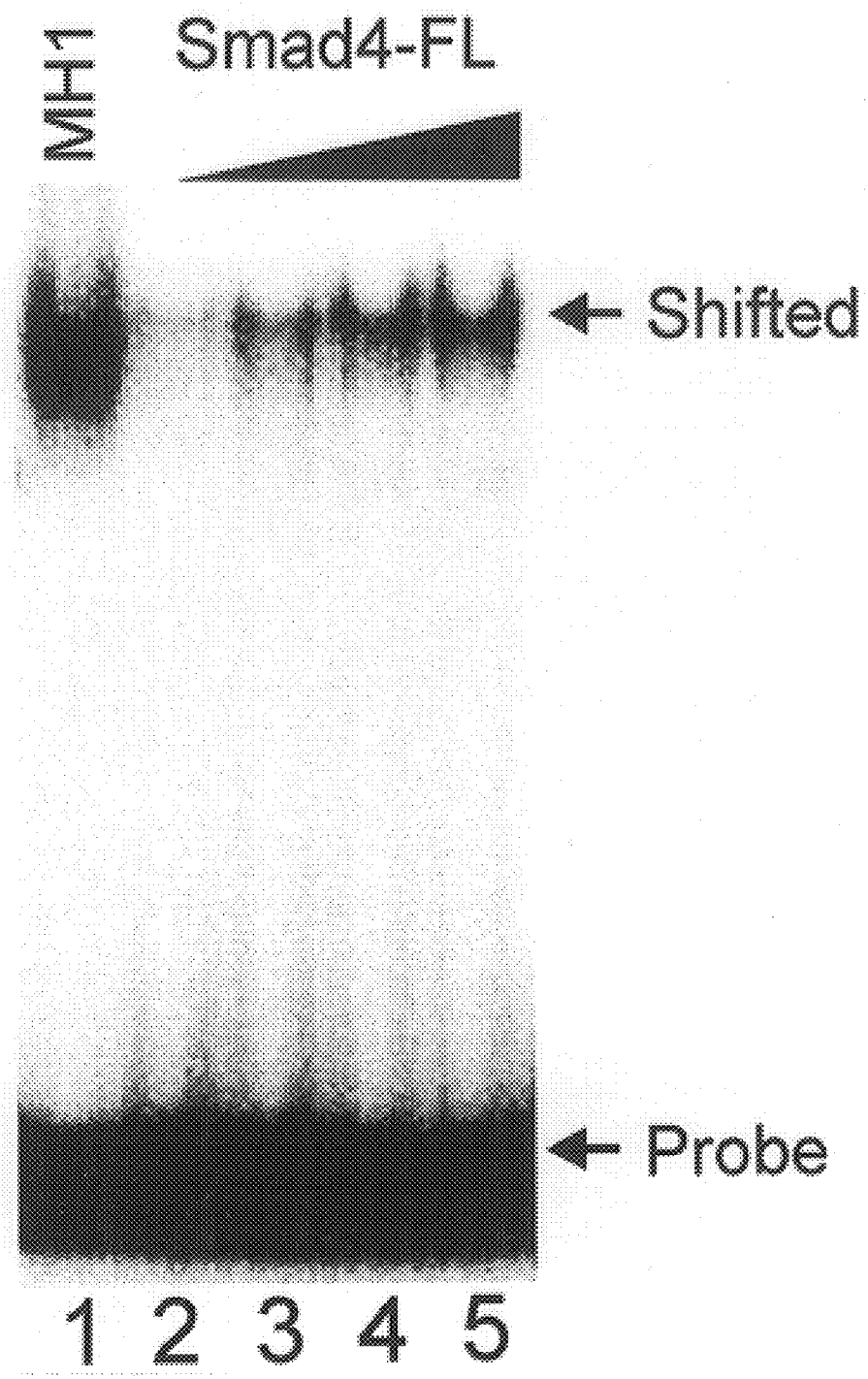

The full length Mad protein did not bind to Vg sequences, suggesting that the carboxyl-terminal half of the protein inhibited binding to its MH1 domain. To determine if the C-terminus of Smad4 similarly inhibited binding to the consensus sequence described above, fusion proteins containing full length (FL) Smad4 were constructed and tested for binding to a SBE probe. Both His-fusion and GST-fusion proteins containing the entire Smad4 protein specifically bound to SBE (FIG. 2B). Additionally, a non-fusion form of the Smad4 protein, made in vitro in a rabbit reticulocyte lysate, also bound specifically to SBE in EMSA experiments (data not shown), ruling out the possibility that contaminating bacterial proteins or GST or His sequences were responsible for the observed binding.

To determine whether the SBE represented the optimal binding site for a full length Smad protein, random oligonucleotides were bound to GST-Smad4/FL and processed using a strategy similar to that described above for the MH1 domains of Smad3 and Smad4. To exclude any effect of the sequences flanking the random nucleotides, the flanking sequences used in this experiment were different from those used to define the binding capacities of the MH1 domains. The sequences of 28 clones containing oligonucleotides which bound to GST-Smad4/FL after three rounds of selection were determined. As indicated in FIG. 4B, the 5'-GTCTAGAC-3' palindrome was again obtained as the predominant species.

EXAMPLE 4

The SBE Confers TGF-β-Responsive Transcription

Figure 3A:
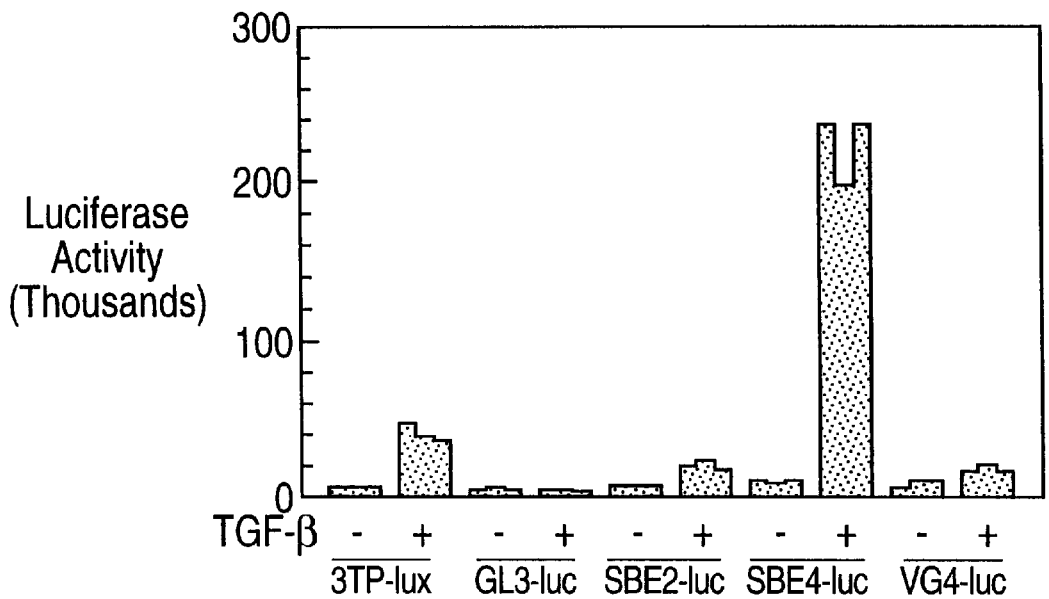
FIG. 3A and 3B. The SBE Confers Smad4Dependent, TGF-β Responsiveness to a Minimal Promoter (FIG. 3A) HaCaT cells were transfected with the indicated plasmids and treated with or without TGF-β. The 3TP-lux plasmid is commonly used to assess TGF-β responsiveness, the GL3 plasmid contains only a minimal promoter, the SBE4-luc plasmid contains four copies of the SBE2-luc plasmid contains two copies of SBE, and the VG4-luc plasmid contains four copies of a Vg sequence previously shown to bind Drosophila Mad (see text). Grouped bars represent luciferase measurements from the same constructs in three separate experiments.

Smad3 and Smad4 have both been implicated as downstream mediators of TGF-β signaling. To test whether the consensus recognized by Smad3 and Smad4 could confer TGF-β responsiveness in vivo, constructs were generated containing repeats of the SBE upstream of a minimal promoter adjoining a luciferase reporter. These constructs and appropriate controls were transfected into HaCaT cells, a human keratinocyte cell line which is TGF-β responsive. Only low levels of reporter activity were detected with a control construct containing only a minimal promoter, and this level was not affected by TGF-β exposure (FIG. 3A). In contrast, the same vector containing four tandem copies of the SBE (pSBE4-luc) was induced 20–25 fold upon treatment of cells with TGF-β. As shown in FIG. 3A, the level of induction achieved with pSBE4-luc was significantly higher than that achieved with the p3TP reporter most commonly used to measure TGF-β responsiveness. Interestingly, a construct containing two copies of SBE (rather than four) was relatively unresponsive to TGF-β (FIG. 3A). Finally, when four tandem repeats of the Vg sequence were substituted for the copies of the SBE, little activation was observed (FIG. 3A).

Figure 3B:
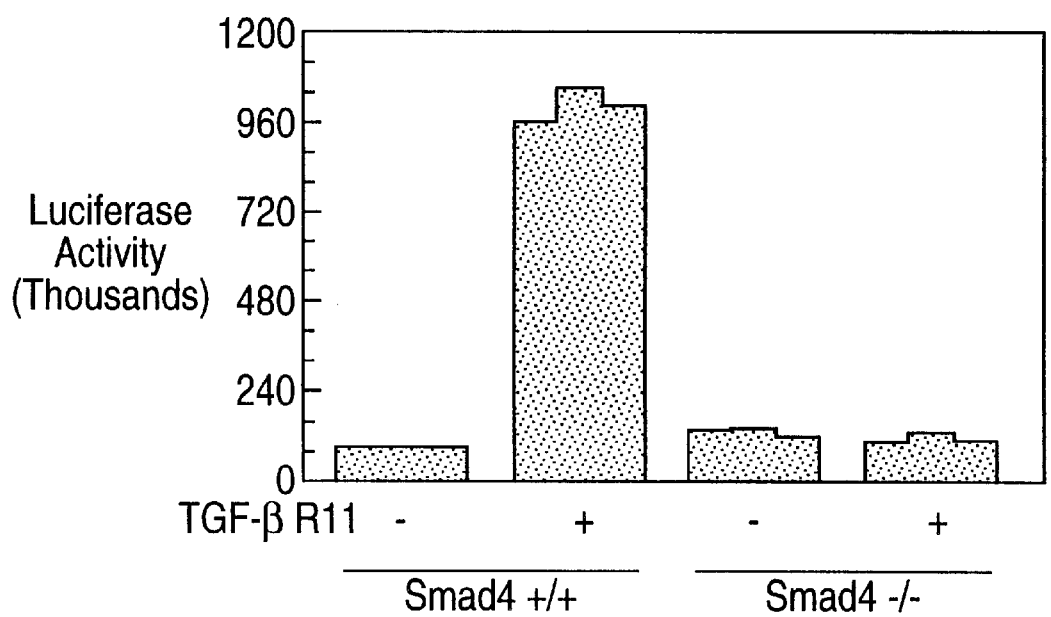

To determine whether Smad4 was required for the TGF-β-dependent activation of pSBE4-luc, experiments were performed with HCT116 cells. HCT116 cells were derived from a colorectal cancer cell line in which the TGF-β-RII genes had been inactivated by naturally occurring mutations. TGF-β responsiveness can be restored in these cells by transfection of an expression vector encoding TGF-β RII. The pSBE4luc reporter was activated by TGF-β in a TGF-β RII-dependent manner in HCT116 cells (FIG. 3B). TGF-β responsiveness of the pSBE4-luc reporter was then assayed in a HCT116 subclone in which both alleles of the Smad4 gene had been inactivated by targeted homologous recombination. Importantly, no TGF-β-dependent activation of pSBE4-luc was observed in these cells, isogeneic to the parental cells except for the inactivation of the endogenous Smad4 gene (FIG. 3B).

The results recorded above demonstrate that neither the Vg nor p3TP-lux-derived sequences represent the optimal binding sites for human Smad proteins. The best match to SBE within the Vg sequences identified by Kim et al. involves 5 of 8 positions (5'-GTCGCGAT-3'). The relatively weak binding of the Vg sequences to human Smad3 and Smad4, plus the inability of the Vg sequences to mediate sequence-specific transactivation (FIG. 3A), suggests that these differences are biologically important. It is possible that Drosophila Mad has a different binding specificity than human Smad proteins. However, the fact that the full length form of Mad could not bind to Vg sequences suggests that this sequence does not represent the optimal binding sequence even for Drosophila proteins.

The Vg sequences bound by the MH1 domain of Drosophila Mad were unrelated to the p3TP-lux sequences found to bind to human Smad4. These 3TP-lux sequences had no significant match to the octameric form of the SBE, though there was a 7-mer (5'-GTCTGAC-3') within the sequences studied by Yingling et al. which matched the SBE if a deletion were permitted at position 5. There was a reasonable match (5'-GTCTGGAC-3') to the SBE within the PAI-1 portion of the 3TP-lux vector distal to the sequences studied by Yingling et al. There were also imperfect matches to the SBE within the regulatory regions of the TGF-β-regulated genes p5 and p21. Further work will be required to determine whether these sites are important for TGF-β responsiveness.

Transfections and Reporter Assays

The new reporters described here were derived from the pGL3 promoter luciferase vector (Promega). Inserts containing SBE or Vg sequences were generated by ligation of concatamerized oligonucleotides to Kpn I-digested pGL3, generating the vectors pSBE2-luc (with two copies of SBE), pSBE4-luc (four copies of the SBE), and pVG4-luc (four copies of the Mad-binding element from Vg). The complementary oligonucleotides used for pSBE2-luc and pSBE4-luc construction were
5'-TAAGTCTAGACGGCAGTCTAGACGTAC-3' and
5'-GTCTAGACTGCCGTCTAGACTTAGTAC-3', while those used for pVG4-luc construction were
5'-GCTTGGCTGCCGTCGCGATTCGTAC-3' and
5'-GAATCGCGACGGCAGCCAAGCGTAC-3'. Transfections were performed in HaCaT or HCT116 cells using FuGene6 (Boehringer Mannheim). TGF-β was added at the time of transfection and luciferase activity determined as described in. For experiments in HCT116 cells, a TGF-β RII expression vector was co-transfected together with each assayed reporter. The 3TP-luc reporter was the generous gift of J. Massagué.

Discussion

Functional Differences Between Smad proteins

Though Smad3 and Smad4 bound the same palindromic octamer, the experiments with Smad4-deficient cells demonstrate that Smad4 was absolutely required for TGF-β responsiveness of a reporter containing SBE sites. Thus Smad3, which was present in the Smad4-deficient cells, could not substitute for Smad4 in these experiments, despite its structural and functional similarities. This result is consistent with previous data demonstrating a unique role for Smad4 in signaling by TGF-β ligands. It was also shown that several copies of the SBE were required for TGF-β activation of a minimal promoter (FIG. 3A). This requirement may reflect the relatively low affinity of single SBE elements for Smad proteins; kinetic measurements show that the dissociation rate for both Smad3 and Smad4 proteins is $>10^{-1}$ (Zawel etal, unpublished data). The formation of a transcriptional complex containing several monomers each of Smad4 and Smad3 would explain the need for multiple SBE sites and the requirement for Smad4. The existence of such a complex is compatible with current models for Smad multimerization.

Smad2 did not specifically bind to the palindrome bound by Smad3 and Smad4 or to any other tested sequence. In view of the homology shared by Smads 2, 3 and 4 in their amino-terminal regions, as well as the functional similarities shared between Smad2 and Smad3, this finding was unexpected. Close inspection of the amino acid alignments, however, revealed a 30 amino acid insertion between codons 79–108 that was unique to Smad2. Perhaps this domain interferes with or interrupts the DNA-binding domain present in Smad3 and 4. Regardless, these results suggest that Smad2 is not likely to be functionally redundant with Smad3 in TGF-β signaling, and predicts that significant phenotypic differences will be found between Smad2 and Smad3 deficient cells.

Phosphorylation of the carboxyl-termini of some Smad proteins by type I receptors has been shown to be the most immediate response to TGF-β and related ligands (references in Introduction). Our results with bacterially-produced Smad proteins show that DNA-binding is not dependent on such phosphorylation. The unimportance of phosphorylation to Smad binding is also consistent with the fact that Smad4 is not phosphorylated upon TGF-β stimulation and in fact lacks the C-terminal SSXS motif required for phosphorylation by the type I receptors. Phosphorylation of Smad proteins is therefore more likely to play a role in modulating protein-protein interactions or nuclear transport than to modulate DNA-binding per se.

Though we have not formally shown that Smad3 or Smad4 activates transcription in vivo, the in vitro binding of these proteins to SBE, the ability of SBE to confer TGF-β-responsiveness to a minimal promoter, the requirement for Smad4 in this responsiveness, and the previously documented presence of a transcriptional activation domain at the carboxyl-terminus of Smad proteins, strongly support this conclusion. A search for genes that contain copies of the SBE within their regulatory regions may illuminate the transcriptional targets of TGF-β and related ligands.

References

Barker, J. C., and Harland, R. M. (1996). A novel mesoderm inducer, Madr2, functions in the activin signal transduction pathway. Genes Dev. 10, 1880–1889.

Carcamo, J., Weiss, F. M., Ventura, F., Wieser, R, Wrana, J. L. Attisano, L. and Massague, J. (1994). Type 1 receptors specify growth-inhibitory and transcriptional responses to TGF-β and activin. Mol. Cell. Biol. 14, 3810–3821.

Carcamo, J., Zentella, A., and Massague, J. (1995). Disruption of TGF-β signaling by a mutation that prevents transphosphorylation within the receptor complex. Mol. Cell. Biol. 15, 1573–1581.

Chen, X., Rubock, M. J., and Whitman, M. (1996). A transcriptional partner for MAD proteins in TGF-β signaling. Nature 383, 691–696.

Chen, X., Weisberg, E., Fridmacher, V., Watanabe, M., Naco, G., and Whitman, M (1997). Smad$^4$ and FAST-1 in the assembly of activin-responsive factor. Nature 389, 85–89.

Eppert, K., Scherer, S. W., Ozcelik H., Pirone, R., Hoodless, P., Kim, H., Tsui, L -C., Bapat, B., Gallinger, S., Andrulis, I. L. et al. (1996). MADR2 maps to 18q21 and encodes a TGF-β-regulated MAD-related protein that is mutated in colorectal carinoma. Cell 86, 543–552.

Hahn, S. A., Hoque, A. T., Moskaluk, C. A, da Costa, L. T., Schutte, M., Rozenblum, E., Seymour, A. B., Weinstein, C. L., Yeo, C. J. Hruban, R. H., and Kern, S. E. (1996). Homozygous deletion map at 18q21.1 in pancreatic cancer. Cancer Res. 56, 490–494.

Hahn, S. A, Schutte, M., Hoque, A. T. M. S., Moskaluk, C. A., Dacosta, L T., Rozenblum, E., Weinstein, C. L. Fischer, A., Yeo, C. J., Hruban, R. H., and Kern, S. E. (1996). Dpc4, a candidate tumor suppressor gene at human chromosome 18q21.1. Science 271, 350–353.

Heidin, C. H., Miyazono, K., and ten Dijke, P. (1997). TGF-β signaling from cell membrane to nucleus through SMAD proteins. Nature 390, 465–471.

Hermeking, H., Lengauer, C., Polyak, K., He, T. -C., Zhang, L. Thiagalingam, S., Kinzler, K. W., and Vogelstein, B. (1997). 14-3-3α is a p53-regulated inhibitor of G2/M progression. Molecular Cell 1, 3–11.

Hoodless, P. (1996). MADR1, a MAD related protein that functions in BMP2 signaling pathways. Cell 85, 489–500.

Hoodless, P. A, and Wrana, J. L. (1998). Mechanism and function of signaling by the TGF-β superfamily. Curr. Top. Microbiol. Immunol. 228, 235–272.

Hoque, A. T., Hahn, S. A., Schutte, M., and Kern, S. E. (1997), DPC4 gene mutation in colitis associated neoplasi. Gut 40, 120–122.

Kim, J., Johnson, K., Chen, H. J., Carroll, S., and Laughon, A. (1997). Drosophila Mad binds to DNA and directly mediates activation of vestigial by Decapentaplegic. Nature 388, 304–308.

Kinzler, K. W., and Vogelstein, B. (1989). Whole genome PCR: application to the identification of sequences bound by gene regulatory proteins. Nucleic Acids Res. 17, 3645–3653.

Kretzschmar, M, Liu, F., Hata, A., Doody, I., and Massague, J. (1997). The TGF-β family mediator Smad1 is phosphorylated directly and activated functionally by the BMP receptor kinase. Genes Dev. 11, 984–995.

Lagna, G., Hata, A., Hemmati-Brivaniou, A., and Massague, J. (1996). Partnership between DPC4 and SMAD proteins in TGF-β signaling pathways. Nature 383, 832–836.

Landesman, Y., Pagano, M., Draetta, G., Rotte, V., Fusenig, N. E., and Kimchi, A. (1992). Modifications of cell cycle controlling nuclear proteins by TGF-β in the HaCaT keratinocyte cell line. Oncogene 7, 1661–1665.

Liu, F., Hata, A., Baker, J. C., Doody, J., Carcamo, J. Harland, R. M., Massague, J. (1996). A human Mad protein acting as a BMP-regulated transcriptional activator. Nature 381, 620–623.

Liu, F., Pouponnot, C., and Massague, J. (1997a). Dual role of the Smad4/DPC4 tumor suppressor in TGF-β-inducible transcriptional complexes. Genes Dev. 11, 3157–3167.

Liu, X., Sun, Yl., Constantinescu, S. N., Karam, E., Weinberg, R. A., and Lodish, H. F. (1997b). TGF-β-induced phosphorylation of Smad3 is required for gowth inhibition and transcriptional induction in epithelial cells. Proc. Natl. Acad. Sci. USA 94, 10669–10674.

Marcias-Silva, M., Abdollah, S., Hoodless, P.A., Pirone, R., Attisano, L., and Wrana, J. L. (1996). MADR2 is a substrate of the TGFβ receptor and its phosphorylation is required for nuclear accumulation and signaling. Cell 87, 1215–1224.

Markowitz, S., Wang, J., Myeroff, L., Parsons, R, Sun, L., Lutterbaugh, J., Fan, R. S. Zborowska, E. Kinzler, K. W., Vogelstein, B., et al. (1995). Inactivation of the type II TGF-β receptor in colon cancer cells with microsatellite instability. Science 268, 1336–1338.

Nakao, A., Imammura, T., Souchelnytskyi, S., Kawabata, M., Ishisaki, A., Oeda, E., Tamaki K,. Hanai, J., Heidin, C. H., Miyazono, K., and ten Dijke, P. (1997). TGF-β receptor-mediated signaling through Smad2, Smad3 and Smad. EMBO J. 16, 5353–5362.

Nakao, A., Roijer, E., Immamura, T., Soucheinytskyi, S., Stenman, G., Heidin, C. H., and ten Dijke, P. (1997). Indentification of Smad2, a human Mad-related protein in the TGF-β signaling pathway. J. Biol. Chem. 272, 2896–2900.

Nakshatri, H., and Bhat-Nakshatri, P. (1997). Differential effect of Nonidet P40 on DNA binding of transcription factors. Anal. Biochm. 249, 103–104.

Oliphant, A. R., Brandl, C. J., and Struhl, K. (1989). Defining the sequence specificity of DNA-binding proteins by selecting binding sites from random-sequence oligonucleotides: analysis of yeast GCN4 protein. Mol. Cell. Biol. 9, 2944–2949.

Parsons, R., Myeroff, L. L., Liu, B., Willson, J. K,. Markowitz, S. D., Kinzler, K. W., and Vogelstein, B. (1995). Microsatellite instability and mutations of the TGF-β type II receptor gene in colorectal cancer. Cancer Res. 55, 5548–5550.

Riggins, G. J., Kinzler, K. W., Vogelstein, B., and Thiagalingam, S. (1996). Mad-related genes in the human. Nat. Genet. 13, 347–349.

Savage, C., Das, P., Finelli, A. -L., Townsend, S. R., Sun, C. Y., Baird, S. E., and Padgett, R. W. (1996). Caenorhabditis elegans genes Sma-2, Sma-3, and Sma-4 define a conserved family of TGF-β pathway components. Proc. Natl. Acad. Sci. USA 93, 790–794.

Sekelsky, J. J., Newfeld, S. J. Raftery, L. A., Chartoff E. H., and Geibart, W. M. (1995). Genetic characterization and cloning of mothers against dpp, a gene required for decapentaplegic function in Drosophila melanogaster. Genetics 139, 1347–1358.

Shi, Y., Hata, A., Lo, R. S., Massague, J., and Pavletich, N. P. 91997). A structural basis for mutational inactivation of the tumor suppressor Smad4. Nature 388, 87–93.

Thiagalingam, S. (1996). Evaluation of chromosome 18q in colorectal cancers. nat. Genet. 13, 343–346.

Wang, J., Sun, L., Myeroff, L. Wang, X., Gentry, L. E., Yang, J., Liang, J., Zborowska, E., Markowitz, S., Willson, J. K., et al. (1995). Demonostration that mutation of the type II TGF-β receptor inactivates its tumor suppressor activity.

Wrana, J. L. Attisano, L., Carcamo, J., Zentella, A, Dooy, J., Laiho, M., Wang, X. F., and Massague, J. (1992). TGF-β signals through a heteromeric protein kinase receptor complex. Cell 71, 1003–1014.

Wu, R. Y., Zhang, Y., Feng, X. H., and Derynck, R. (1997). Heteromeric and homomeric interactions correlate with signaling activity and functional cooperativity of Smad3 and Smad4/DPC4. Mol. Cell. Biol. 17, 2521–2528.

Yingling, J. M., Datto, M. B., Wong, C., Frederick, J. P., Liberati, N. T., and Wang, X. F. (1997). Tumor suppressor Smad4 is a TGF-β-inducible DNA binding protein. Mol. Cell. Biol. 17, 7019–7028.

Zhang, Y., Feng, X., Wu, R, and Derynck, R. (1996) Receptor-associated Mad homologues synergize as effectors of the TGF-β response. Nature 383, 168–172.

Zhou, S., Buckhaults, P., Zawel, L., Bunz, F., Riggins, G., Dai, J. L. Kern, S. E., Kinzler, K. W., and Vogeistein, B. (1998). Targeted deletion of Smad4 shows it is required for TGF- and activin signaling colorectal cancer cells. Proc. Natl. Acad Sci. USA 95, in press.

We claim:

1. An isolated subgenomic polynucleotide comprising at least 2 copies of a SMAD binding element as shown in any of SEQ ID NOs: 1–27 (FIGS. 1B and 1D), wherein at least 2 of the copies of the SMAD binding element are separated by less than 50 nucleotides.

2. The polynucleotide of claim 1 wherein at least 2 copies of the SMAD binding element are separated by less than 20 nucleotides.

3. The polynucleotide of claim 1 which comprises at least 4 copies of the SMAD binding element.

4. The polynucleotide of claim 1 which is double stranded.

5. The polynucleotide of claim 1 which is attached to a solid support.

6. The polynucleotide of claim 1 which is attached to an insoluble polymer.

7. A nucleic acid construct comprising at least one SMAD binding element as shown in any of SEQ ID NOs: 1–27, a minimal promoter, and a reporter gene, wherein the minimal promoter is upstream from the reporter gene, wherein the minimal promoter regulates transcription of the reporter gene.

8. The nucleic acid construct of claim 7 which comprises at least 2 copies of the SMAD binding element.

9. The nucleic acid construct of claim 7 which comprises at least 3 copies of the SMAD binding element.

10. The nucleic acid construct of claim 7 which comprises at least 4 copies of the SMAD binding element.

11. A method of pre-screening agents for use in cancer therapy, comprising:

measuring binding of a SMAD3 or SMAD4 protein to a DNA molecule comprising a SMAD binding element;

measuring binding of the SMAD3 or SMAD4 protein to the DNA molecule in the presence of a test substance; and comparing amount of binding of the SMAD3 or SMAD4 protein in the presence of the test substance to amount of binding of the SMAD3 or SMAD4 protein in the absence of the test substance, a test substance which increases the amount of binding being a candidate for use in cancer therapy.

12. The method of claim 11 wherein the SMAD3 or SMAD4 protein is encoded by a mutant gene found in cancer cells of a patient.

13. The method of claim 11 wherein the SMAD3 or SMAD4 protein is wild-type.

14. A method of pre-screening agents for use in cancer therapy, comprising:

contacting a transfected cell with a test substance, the transfected cell containing a SMAD3 or SMAD4 protein and a reporter gene construct comprising a reporter gene which encodes an assayable product, at least one copy of a SMAD binding element, and a minimal promoter upstream from and regulating transcription of the reporter gene; and determining whether the amount of expression of the reporter gene is altered by the test substance, a test substance which increases the amount of expression of the reporter gene being a candidate for use in cancer therapy.

15. The method of claim 14 wherein the SMAD3 or SMAD4 protein is encoded by a mutant gene found in cancer cells of a patient.

16. The method of claim 14 wherein the SMAD3 or SMAD4 protein is wild-type.

17. The method of claim 14 wherein the transfected cell is in culture.

18. The method of claim 14 wherein the transfected cell is in a mammalian body.

19. A method of pre-screening potential therapeutic agents, comprising:

contacting a transfected cell with a test substance and TGFβ, the transfected cell containing a SMAD3 or SMAD4 protein and a reporter gene construct comprising a reporter gene which encodes an assayable product, at least one copy of a SMAD binding element, and a minimal promoter upstream from and regulating transcription of the reporter gene; and determining whether the amount of expression of the reporter gene is altered by the test substance, a test substance which decreases the amount of expression of the reporter gene being a candidate for inhibiting apoptosis.

20. The method of claim 19 wherein the SMAD3 or SMAD4 protein is encoded by a mutant gene found in cancer cells of a patient.

21. The method of claim 19 wherein the SMAD3 or SMAD4 protein is wild-type.

22. The method of claim 19 wherein the transfected cell is in culture.

23. The method of claim 19 wherein the transfected cell is in a mammalian body.

24. A method of pre-screening agents for use in cancer therapy, comprising:

adding RNA polymerase and ribonucleotides to a transcription construct, the transcription construct comprising a reporter gene which encodes an assayable product, at least one copy of a SMAD binding element, and a minimal promoter upstream from and controlling transcription of the reporter gene, the step of adding being effected in the presence and absence of a test substance; and determining whether the amount of transcription of the reporter gene is altered by the presence of the test substance, a test substance which alters the amount of transcription of the reporter gene being a candidate for use in cancer therapy.

25. A method of pre-screening oligonucleotides for use in cancer therapy, comprising:

adding (a) a SMAD3 or SMAD4 protein which is encoded by a mutant gene found in a cancer patient and (b) a preparation of random oligonucleotides to (c) a DNA fragment comprising at least one copy of a SMAD Binding Element immobilized on a solid support, to bind SMAD3 or SMAD4 protein to the DNA fragment immobilized on a solid support; and recovering oligonucleotides from the preparation which bound to SMAD3 or SMAD4 which bound to the DNA fragment immobilized on the solid support.

26. A method for detecting the presence of wild-type SMAD3 or SMAD4 protein in a cell, comprising the steps of:

contacting a DNA molecule comprising at least one SMAD binding element with a cell lysate from a tissue of a human, to bind the DNA molecule to wild-type SMAD3 or SMAD4 present in the cell lysate;

detecting the presence of wild-type SMAD3 or SMAD4 protein in the cell by detecting binding of the proteins to the DNA molecule.

27. The method of claim 26 wherein the DNA molecule comprises at least two copies of the SMAD binding element.

28. The method of claim 26 wherein the DNA molecule comprises at least three copies of the SMAD binding element.

29. The method of claim 26 wherein the DNA molecule comprises at least four copies of the SMAD binding element.

30. The method of claim 26 wherein the DNA molecule is labeled with a detectable moiety selected from the group consisting of: a radioactive moiety, a colorimetric moiety, or a fluorescent moiety.

31. The method of claim 26 wherein the step of detecting binding of the DNA fragment to wild-type SMAD3 or SMAD4 comprises:

contacting SMAD3 or SMAD4 protein with anti-SMAD3 or SMAD4 monoclonal antibodies, and detecting the monoclonal antibodies.

32. A method of detecting the presence of a wild-type SMAD3 or SMAD4 protein in a cell, comprising the steps of:

providing a histological section from a human;

incubating the section with a detectably-labeled DNA molecule comprising at least one SMAD binding element, to bind the DNA molecule to wild-type SMAD3 or SMAD4 present in the histological sample;

removing unbound DNA molecule from the histological section; and determining the amount of the DNA molecule which is bound to the histological sample.

33. The method of claim 32 wherein the DNA molecule is labeled with a detectable moiety selected from the group consisting of: a radioactive moiety, a colorimetric moiety, or a fluorescent moiety.

34. A method of identifying compounds which specifically bind to a SMAD binding element, comprising the steps of:

contacting a DNA molecule comprising at least one SMAD binding element with a test compound, to bind the test compound to the DNA molecule;

determining the amount of test compound which is bound to the DNA molecule.

35. A method of identifying compounds which specifically bind to SMAD binding elements, comprising the steps of:

contacting an immobilized DNA molecule comprising a SMAD binding element with both a test compound and wild-type SMAD3 or SMAD4 protein to bind the wild-type SMAD3 or SMAD4 protein to the DNA molecule;

determining the amount of wild-type SMAD3 or SMAD4 protein which is bound to the DNA molecule, inhibition of binding of wild-type SMAD3 or SMAD4 protein by the test compound indicating binding of the test compound to the SMAD binding element.

36. A method for detecting a SMAD3 or SMAD4 gene in a human cell, comprising:

obtaining a nucleic acid molecule encoding a SMAD3 or SMAD4 protein from a human cell;

expressing a SMAD3 or SMAD4 protein from the nucleic acid molecule;

contacting the expressed SMAD3 or SMAD4 protein with a reporter construct comprising:

at least one SMAD binding element, a minimal promoter, and a reporter gene, wherein the minimal promoter is upstream from the reporter gene, wherein the minimal promoter regulates transcription of the reporter gene;

monitoring expression of the product of the reporter gene.

37. The method of claim 36 wherein the step of expressing is performed in a transfected cell.

38. The method of claim 36 wherein the step of expressing is performed in a cell-free system.

39. The method of claim 36 wherein the step of contacting is performed in a transfected cell.

40. The method of claim 36 wherein the step of contacting is performed in a cell-free system.

41. The method of claim 36 wherein the steps of expressing and contacting are performed in a transfected cell.

42. A method for detecting a SMAD3 or SMAD4 gene in a human cell, comprising:

obtaining a nucleic acid molecule encoding a SMAD3 or SMAD4 protein from a human cell;

expressing a SMAD3 or SMAD4 protein from the nucleic acid molecule;

contacting the expressed SMAD3 or SMAD4 protein with an isolated subgenomic polynucleotide comprising a SMAD binding element;

monitoring binding of the expressed SMAD3 or SMAD4 to the isolated subgenomic polynucleotide.

43. The method of claim 42 wherein the step of expressing is performed in a transfected cell.

44. The method of claim 42 wherein the step of expressing is performed in a cell-free translation system.

45. The method of claim 11 wherein the SMAD binding element is selected from the group consisting of SEQ ID NOs: 1–27.

46. The method of claim 14 wherein the SMAD binding element is selected from the group consisting of SEQ ID NOs:1–27.

47. The method of claim 19 wherein the SMAD binding element is selected from the group consisting of SEQ ID NOs: 1–27.

48. The method of claim 24 wherein the SMAD binding element is selected from the group consisting of SEQ ID NOs: 1–27.

49. The method of claim 25 wherein the SMAD binding element is selected from the group consisting of SEQ ID NOs:1–27.

50. The method of claim 26 wherein the SMAD binding element is selected from the group consisting of SEQ ID NOs:1–27.

51. The method of claim 32 wherein the SMAD binding element is selected from the group consisting of SEQ ID NOs:1–27.

52. The method of claim 34 wherein the SMAD binding element is selected from the group consisting of SEQ ID NOs: 1–27.

53. The method of claim 35 wherein the SMAD binding element is selected from the group consisting of SEQ ID NOs: 1–27.

54. The method of claim 36 wherein the SMAD binding element is selected from the group consisting of SEQ ID NOs:1–27.

55. The method of claim 42 wherein the SMAD binding element is selected from the group consisting of SEQ ID NOs: 1–27.

56. The polynucleotide of claim 1 wherein at least 2 copies of the SMAD binding element are separated by less than 10 nucleotides.

57. The polynucleotide of claim 1 wherein at least 2 copies of the SMAD binding element are immediately adjacent.

* * * * *